(12) United States Patent
Wells et al.

(10) Patent No.: US 8,349,300 B2
(45) Date of Patent: Jan. 8, 2013

(54) PERSONAL CARE COMPOSITIONS CONTAINING AT LEAST TWO CATIONIC POLYMERS AND AN ANIONIC SURFACTANT

(75) Inventors: Robert Lee Wells, Cincinnati, OH (US); Mark Anthony Brown, Union, KY (US); Douglas Allan Royce, Sunman, IN (US); Brandon Scott Lane, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 459 days.

(21) Appl. No.: 12/103,902

(22) Filed: Apr. 16, 2008

(65) Prior Publication Data

US 2008/0317698 A1 Dec. 25, 2008

Related U.S. Application Data

(60) Provisional application No. 60/925,352, filed on Apr. 19, 2007.

(51) Int. Cl.
*A61Q 5/02* (2006.01)
*A61Q 5/12* (2006.01)

(52) U.S. Cl. ............... 424/70.122; 424/70.1; 424/70.11; 424/70.22

(58) Field of Classification Search .................. None
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Kosmin | |
| 2,826,551 A | 3/1958 | Geen | |
| 3,929,678 A | 12/1975 | Laughlin et al. | |
| 3,932,610 A | 1/1976 | Rudy et al. | |
| 3,964,500 A | 6/1976 | Drakoff | |
| 4,364,837 A | 12/1982 | Pader | |
| 5,104,646 A | 4/1992 | Bolich, Jr. et al. | |
| 5,106,609 A | 4/1992 | Bolich, Jr. et al. | |
| RE34,584 E | 4/1994 | Grote et al. | |
| 5,876,705 A * | 3/1999 | Uchiyama et al. | 424/70.12 |
| 6,355,234 B1 * | 3/2002 | Birtwistle et al. | 424/70.27 |
| 7,268,104 B2 | 9/2007 | Krzysik et al. | |
| 7,527,077 B2 | 5/2009 | McCall et al. | |
| 7,531,497 B2 | 5/2009 | Midha et al. | |
| 7,700,528 B2 | 4/2010 | Wei et al. | |
| 7,811,552 B2 * | 10/2010 | Maubru et al. | 424/70.12 |
| 2003/0108501 A1 | 6/2003 | Hofrichter et al. | |
| 2003/0223951 A1 | 12/2003 | Geary et al. | |
| 2004/0219119 A1 | 11/2004 | Wei et al. | |
| 2004/0223991 A1 | 11/2004 | Wei et al. | |
| 2005/0143268 A1 | 6/2005 | Midha et al. | |
| 2005/0143269 A1 | 6/2005 | Wei et al. | |
| 2005/0220736 A1 | 10/2005 | Polonka et al. | |
| 2005/0276768 A1 | 12/2005 | Wei et al. | |
| 2006/0078524 A1 | 4/2006 | Midha et al. | |
| 2006/0078527 A1 | 4/2006 | Midha et al. | |
| 2006/0099167 A1 | 5/2006 | Staudigel et al. | |
| 2007/0009463 A1 | 1/2007 | Niebauer et al. | |
| 2007/0009472 A1 | 1/2007 | Niebauer et al. | |
| 2007/0010410 A1 | 1/2007 | Niebauer et al. | |
| 2007/0014823 A1 | 1/2007 | Iwata | |
| 2007/0095721 A1 | 5/2007 | Davis et al. | |
| 2007/0280976 A1 | 12/2007 | Taylor et al. | |
| 2008/0029514 A1 | 2/2008 | Davis et al. | |
| 2008/0029515 A1 | 2/2008 | Davis et al. | |
| 2008/0196787 A1 | 8/2008 | Comstock et al. | |
| 2010/0006573 A1 | 1/2010 | Davis et al. | |

FOREIGN PATENT DOCUMENTS

| | | |
|---|---|---|
| CN | 1558747 A | 12/2004 |
| GB | 849433 | 9/1960 |
| WO | WO 2006/052580 | 5/2006 |
| WO | WO 2007/065537 A | 6/2007 |

OTHER PUBLICATIONS

U.S. Appl. No. 29/241,857, filed Dec. 3, 2008, Comstock.
U.S. Appl. No. 29/266,284, filed Sep. 18, 2006, Comstock.
U.S. Appl. No. 29/266,287, filed Sep. 18, 2006, Comstock.
U.S. Appl. No. 29/266,288, filed Sep. 18, 2006, Comstock.
Burgess, D. J., "Practical Analysis of Complex Coacervate Systems," *J. of Colloid and Interface Science*, vol. 140, No. 1, Nov. 1990, pp. 227-238.
International Search Report, PCT/IB2008/051504, dated Apr. 18, 2008.
J. Caelles, et al., "Anionic and Cationic Compounds in Mixed Systems," Cosmetics & Toiletries, vol. 106, Apr. 1991, pp. 49-54.
Laughlin, R. G. (1994) The Aqueous Phase Behavior of Surfactants, 182, 8.2.
Solarek, D. B., Cationic Starches in Modified Starches: Properties and Uses, Wurzburg, O.B., Ed., CRC Press, Inc., Boca Raton, Florida 1986, pp. 113-125.
Van Oss, C. J., "Coacervation, Complex Coacervation and Flocculation," *J. Dispersion Science and Technology*, vol. 9 (5,6), 1988-89, pp. 561-573.

\* cited by examiner

*Primary Examiner* — Jyothsna Venkat
(74) *Attorney, Agent, or Firm* — Angela K. Haughey

(57) ABSTRACT

A personal cleansing composition comprising:
a. from about 5% to about 50% by weight of an anionic detersive surfactant;
b. from about 0.025% to about 5% by weight of a first cationic polymer having a cationic charge density of less than about 4 meq/gm, wherein said first cationic polymer forms an isotropic coacervate;
c. from about 0.025% to about 5% by weight of a second cationic polymer having a cationic charge density of greater than or equal to about 4 meq/gm, wherein said second cationic polymer forms a lyotropic liquid crystal coacervate; and
d. from about 20% to about 94% by weight of water.

6 Claims, No Drawings

PERSONAL CARE COMPOSITIONS CONTAINING AT LEAST TWO CATIONIC POLYMERS AND AN ANIONIC SURFACTANT

CROSS REFERENCE TO RELATED APPLICATION

This application claims the benefit of U.S. Provisional Application No. 60/925,352 filed Apr. 19, 2007.

FIELD OF THE INVENTION

The present invention relates to conditioning personal care compositions with improved conditioning performance which comprise select cationic polymers.

BACKGROUND OF THE INVENTION

Conditioning personal care compositions comprising various combinations of detersive surfactant and hair conditioning agents are known. These personal care products typically comprise an anionic detersive surfactant in combination with a conditioning agent such as silicone, hydrocarbon oil, fatty esters, or combinations thereof. These personal care compositions have become more popular among consumers as a means of conveniently obtaining hair conditioning and hair cleansing performance all from a single hair care product.

Many personal care compositions, however, do not provide sufficient deposition of conditioning agents onto hair or skin during application. Obtaining good deposition of a conditioning agent onto hair is complicated by the action of detersive surfactants in the personal care composition. Detersive surfactants are designed to carry away or remove, oil, grease, dirt, and particulate matter from the hair and scalp. In doing so, the detersive surfactants can also interfere with deposition of the conditioning agent, and carry away both deposited and non deposited conditioning agent during rinsing. This reduces deposition of the conditioning agent onto the hair after rinsing, thus reducing hair conditioning performance. Without sufficient deposition of the conditioning agent on the hair, relatively high levels of conditioning agents may be needed in the personal care composition to provide adequate hair conditioning performance. Such high levels of a conditioning agent, however, can increase raw material costs, reduce lathering, and present product stability concerns.

One known method for improving deposition of a hair conditioning agent onto hair involves the use of certain cationic polymers. Such cationic polymers may form coacervate phases which aid deposition of conditioning agents and provide good wet hair conditioning benefits such as wet hair feel, detangling, and wet combing ease.

One class of cationic polymers comprises high charge density polymers which form a lyotropic liquid crystal coacervate in the presence of an anionic surfactant. Such polymers are characterized by excellent wet combing benefits when used in shampoo compositions, even in the absence of secondary conditioning agents. When conditioning agents are used, liquid crystal coacervates aid in deposition of large particle size silicone to skin and hair. However, liquid crystal forming polymers do not provide an extended soft wet conditioning and feel throughout the rinse process—as would be expected by a consumer from a desirable conditioning shampoo.

Another class of cationic polymers comprises low charge density cationic polymers which form isotropic coacervates upon dilution of the personal care composition with water. They are often characterized by their favorable wet conditioning and feel, even in the absence of conditioning agents. When conditioning agents are used, isotropic coacervates have been found to aid deposition of small particle size silicone, to skin and hair. However, such low charge density cationic polymers lack the level of wet combing benefit delivered by lyotropic liquid crystal coacervate forming cationic polymers.

Furthermore, formulation of compositions comprising both lyotropic liquid crystal coacervate and isotropic coacervate has been, thus far, unsuccessful. Previous attempts to formulate such compositions have resulted in the destruction of one, or both, of the coacervate phases upon combination.

Based on the foregoing, there still exists a need for a personal care composition with both excellent wet conditioning and wet combing benefits.

SUMMARY OF THE INVENTION

The present invention relates to a personal care composition comprising:
a. from about 5% to about 50% by weight of an anionic detersive surfactant;
b. from about 0.025% to about 5% by weight of a first cationic polymer having a cationic charge density of less than about 4 meq/gm, wherein said first cationic polymer forms an isotropic coacervate;
c. from about 0.025% to about 5% by weight of a second cationic polymer having a cationic charge density of greater than or equal to about 4 meq/gm, wherein said second cationic polymer forms a lyotropic liquid crystal coacervate; and
d. from about 20% to about 94% by weight of water.

DETAILED DESCRIPTION OF THE INVENTION

The personal care compositions of the present invention can comprise, consist of, or consist essentially of the essential elements and limitations of the invention described herein, as well any of the additional or optional ingredients, components, or limitations described herein.

It has been surprisingly discovered that by combining low charge density cationic polymers which form isotropic coacervates with higher charge density cationic polymers, which combine with an anionic surfactant to form lyotropic liquid crystals in a personal care composition, provides both excellent wet hair feel and excellent wet combing benefits.

Furthermore, it has been discovered that in order for the lyotropic liquid crystal coacervate and isotropic coacervates to coexist in a personal care composition the high charge density liquid crystal forming polymer must be premixed with an anionic surfactant prior to the addition of the low charge density isotropic coacervate forming polymer. A detailed description of the formulation process is described herein.

Moreover, without being limited to a particular theory, it appears that when dispersed conditioning agent particles are added to the matrix, the concentrated polymer lyotropic liquid crystal phase and isotropic coacervate phase provide an improved mechanism for conditioning agent deposition, resulting in an overall conditioning benefit.

The liquid crystalline state exists structurally between the solid crystalline phase and the liquid phase (i.e. an intermediate between the three dimensionally ordered crystalline state and the completely disordered liquid state).

In one embodiment, the personal cleansing compositions include an anionic surfactant, a cationic polymer having a cationic charge density of less than about 4 meq/gm, a cationic polymer having a cationic charge density of greater than or equal to about 4 meq/gm, and water. Each of these components, as well as other preferred or optional components are described in detail hereinafter.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

The term "amphiphilic" as used herein, refers to complexes having both hydrophilic and hydrophobic properties.

The term "isotropic" as used herein, means a particular phase structure of coacervate wherein the structure is "[random or disordered] along any three orthogonal directions in space, and is therefore dark or 'nonbirefringent' when viewed between crossed polarized light. (One direction is 'orthogonal' to another if the vector component of the first, in the direction of the second, is zero.)" (Laughlin, R. G. (1994) The Aqueous Phase Behavior of Surfactants, 182, 8.2).

The term "liquid crystal" as used herein, means a material having phases that are ordered and/or crystalline in only one or two of their three possible orthogonal directions and are disordered (random and/or liquid-like) in the other dimensions.

The term "lyotropic" as used herein, means that the ordering effects of a material are induced by changing both its concentration and temperature. Lyotropic liquid crystals are in the class of amphiphilic materials.

The term "neat" as used herein, means the unadulterated form of the present composition (i.e. prior to altering of the composition through dilution with water).

The term, "nonvolatile" refers to any material having little or no significant vapor pressure under ambient conditions, and a boiling point under one atmosphere (atm) preferably at least about 250° C. The vapor pressure under such conditions is preferably less than about 0.2 mm.

The term "water soluble" as used herein, means that the polymer is soluble in water in the present composition. In general, the polymer should be soluble at 25° C. at a concentration of 0.1% by weight of the water solvent, preferably at 1%, more preferably at 5%, more preferably at 15%.

Detersive Surfactant Component

The personal care compositions comprise an anionic detersive surfactant component to provide cleaning performance to the composition. The anionic detersive surfactant component in turn comprises anionic detersive surfactant, zwitterionic or amphoteric detersive surfactant which has an attached group that is anionic at the pH of the composition, or a combination thereof, preferably anionic detersive surfactant. Such surfactants should be physically and chemically compatible with the essential components described herein, or should not otherwise unduly impair product stability, aesthetics or performance.

Suitable anionic detersive surfactant components include those which are known for use in hair care or other personal care cleansing compositions. The concentration of the anionic surfactant component in the personal care composition should be sufficient to provide the desired cleaning and lather performance, and generally range from about 5% to about 50%, preferably from about 8% to about 30%, more preferably from about 10% to about 25%, even more preferably from about 12% to about 20%, by weight of the composition.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the personal care composition herein include those which are known for use in hair care or other personal care cleansing composition, and which contain a group that is anionic at the pH of the personal care composition. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. Nos. 5,104,646 and 5,106,609.

The personal care compositions may further comprise additional surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the personal care composition, or does not otherwise unduly impair product performance, aesthetics or stability. The concentration of the optional additional surfactants in the personal care composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the personal care compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

Naturally Derived Cationic Polymer

The personal care compositions of the present invention comprise a first cationic polymer which is a low charge density cationic polymer. In a preferred embodiment, the first cationic polymer is a naturally derived cationic polymer. The term, "naturally derived cationic polymer" as used herein, refers to cationic polymers which are obtained from natural sources. The natural sources may be polysaccharide polymers. Therefore, the naturally derived cationic polymer may be selected from celluloses, starches, guars, non-guar-galactomannans, and other sources found in nature.

The first cationic polymer has a molecular weight of from about 1,000 to about 10,000,000, and a cationic charge density of at least about 0.2 meq/g, more preferably at least about 0.5 meq/g. The first cationic polymer also has a charge density of less than about 4.0 meq/gm, and more preferably less than or equal to about 2 meq/gm. The polymers are typically present in a concentration of from about 0.025% to about 5%, and more preferably from about 0.10% to about 2% by weight of the personal care composition. The first cationic polymers form an isotropic coacervate in the neat composition or upon dilution with water. The isotropic coacervate aids in deposition of optional small particle size conditioning agents, and provides excellent wet conditioning performance. Such deposition and wet conditioning enhancement result in hair feel, shine, and other appreciable benefits.

The cationic polymers herein are either soluble in the personal care composition, or are soluble in a complex coacervate phase in the personal care composition formed by the cationic polymer and the anionic detersive surfactant component described hereinbefore. Complex coacervates of the cationic polymer can also be formed with other charged materials, such as anionic polymers, in the personal care composition.

Isotropic coacervate formation is dependent upon a variety of criteria such as molecular weight, component concentration, and ratio of interacting ionic components, ionic strength (including modification of ionic strength, for example, by addition of salts), charge density of the cationic and anionic components, pH, temperature, and the aforementioned surfactant system. Isotropic coacervate systems and the effect of these parameters have been described, for example, by J. Caelles, et al., "Anionic and Cationic Compounds in Mixed Systems", Cosmetics & Toiletries, Vol. 106, April 1991, pp 49-54, C. J. van Oss, "Coacervation, Complex Coacervation and Flocculation", J. Dispersion Science and Technology, Vol. 9 (5, 6), 1988-89, pp 561-573, and D. J. Burgess, "Practical Analysis of Complex Coacervate Systems", J. of Colloid and Interface Science, Vol. 140, No. 1, November 1990, pp 227-238.

It is believed to be particularly advantageous for the first cationic polymer to be present in the personal care composition in an isotropic coacervate phase, or to form an isotropic coacervate phase upon application or rinsing of the composition to or from the hair. Complex isotropic coacervates are believed to more readily deposit on the hair than a dissolved polymer. Thus, in general, it is preferred that the first cationic polymer exist in the personal care composition as an isotropic coacervate phase or form an isotropic coacervate phase upon dilution.

Techniques for analysis of formation of complex isotropic coacervates are known in the art. For example, microscopic analyses of the personal care compositions, at any chosen stage of dilution, can be utilized to identify whether an isotropic coacervate phase has formed. Such isotropic coacervate phases will be identifiable as an additional emulsified phase in the composition. The use of dyes can aid in distinguishing the isotropic coacervate phase from other insoluble phases dispersed in the personal care composition.

Cationic Polysaccharide Polymers

The personal care compositions of the present invention may include a naturally derived cationic polymer which is a cationic polysaccharide polymer. Cationic polysaccharide polymers encompass cellulose polymers, starch polymers, and polymers made up of multiple monosaccharides joined together by glycosidic linkages. Suitable polysaccharide cationic polymers include those which conform to the following formula:

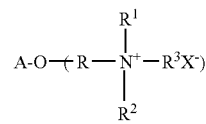

wherein A is an anhydroglucose residual group, such as a cellulose anhydroglucose residual; R is an alkylene oxyalkylene, polyoxyalkylene, or hydroxyalkylene group, or combination thereof; R1, R2, and R3 independently are alkyl, aryl, alkyl aryl, aryl alkyl, alkoxyalkyl, or alkoxyaryl groups, each group containing up to about 18 carbon atoms, and the total No of carbon atoms for each cationic moiety (i.e., the sum of carbon atoms in R1, R2 and R3) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA) under the trade name, Ucare Polymer KG-30M, having a cationic charge density of about 1.9 meq/gm.

Cationically Modified Starch Polymer

The personal care compositions may comprise a naturally derived cationic polymer which is a water-soluble cationically modified starch polymer. As used herein, the term, "cationically modified starch", refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starches having a net positive charge. The term "amphoterically modified starch" refers to a starch hydrolysate to which a cationic group and an anionic group are added.

A method of chemically modifying the charge densities of the cationically modified starch polymers includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers may comprise maltodextrin. Thus, in one embodiment of the present invention, the cationically modified starch polymers may be further characterized by a Dextrose Equivalance ("DE") value of less than about 35, and more preferably from about 1 to about 20. The DE value is a measure of the reducing equivalence of the hydrolyzed starch referenced to dextrose and expressed as a percent (on dry basis). Starch completely hydrolyzed to dextrose has a DE value of 100, and unhydrolyzed starch has a DE value of 0. A suitable assay for DE value includes one described in "Dextrose Equivalent", Standard Analytical Methods of the Member Companies of the Corn Industries Research Foundation, 1st ed., Method E-26. Additionally, the cationically modified starch polymers may comprise a dextrin. Dextrin is typically a pyrolysis product of starch with a wide range of molecular weights.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof. Waxy corn starch is preferred.

In one embodiment of the present invention, cationically modified starch polymers are selected from degraded cationic maize starch, cationic tapioca, cationic potato starch, and mixtures thereof. In another embodiment, cationically modified starch polymers are cationic corn starch.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers in the present invention may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

Suitable cationically modified starches are available from known starch suppliers, such as National Starch. Also suitable for use in the present invention is nonionic modified starch that could be further derivatized to a cationically modified starch as is known in the art. Other suitable modified starch starting materials may be quaternized, as is known in the art, to produce a cationically modified starch polymer suitable for use in the present invention.

One method of conducting starch degradation involves preparing a starch slurry by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

Cationic Galactomannan Polymer

The personal care compositions may comprise a naturally derived cationic polymer which may be a guar or non-guar galactomannan polymer. In one embodiment, the galactomannan polymer is a polymer derivative having a mannose to galactose ratio of 2:1 or greater, on a monomer to monomer basis, and the galactomannan polymer derivative is selected from the group consisting of a cationic galactomannan polymer derivative and an amphoteric galactomannan polymer derivative having a net positive charge. The term "galactomannan polymer derivative", means a compound obtained from a galactomannan polymer (ie. a galactomannan gum) which is chemically modified. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of µ (1-4) glycosidic linkages. The galactose branching arises by way of an µ (1-6) linkage. The ratio of mannose monomers to galactose monomers varies according to the species of the plant and also is affected by climate. Guar is an example of one type of a galactomannan polymer, specifically having a mannose to galactose ratio of 2 monomers of mannose to 1 monomer of galactose. In one embodiment, the galactomannan polymer derivatives have a ratio of mannose to galactose of greater than 2:1 on a monomer to monomer basis (i.e., non-guar galactomannan polymers). Preferably, the ratio of mannose to galactose is greater than about 3:1, and more preferably the ratio of mannose to galactose is greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to tara gum (3 parts mannose/1 part galactose), locust bean or carob (4 parts mannose/1 part galactose), and cassia gum (5 parts mannose/1 part galactose). Herein, the term "non-guar galactomannan polymer derivatives" refers to cationic polymers which are chemically modified from a non-guar galactomanan polymer. A preferred non-guar galactomannan polymer derivative is cationic cassia and is sold under the trade name Cassia EX-906, which is commercially available from Noveon Inc.

Suitable galactomannan polymer derivatives are described in U.S. Patent Publication No. 2006/0099167A1 to Staudigel et al.

Synthetic Cationic Polymer

The personal care compositions of the present invention comprise a second cationic polymer having a high charge density. In a preferred embodiment, the second cationic polymer is a synthetic cationic polymer. The second cationic polymer, in combination with the anionic surfactant component, forms lyotropic liquid crystals. The polymers can be formulated in a stable personal care composition that provides improved conditioning performance, and also provides improved deposition of the optional large particle size conditioning agents (described herein) onto hair. In one embodiment, the synthetic cationic polymer may be formed from i) one or more cationic monomer units, and optionally
ii) one or more momomer units bearing a negative charge, and/or
iii) a nonionic momomer, wherein the subsequent charge of the copolymer is positive. The ratio of the three types of monomers is given by m, p and q where m is the number of cationic monomers, p the No of momomers bearing a negative charge and q is the number of nonionic momomers.

The concentration of the second cationic polymer in the personal care composition ranges about 0.025% to about 5%, preferably from about 0.1% to about 3%, more preferably from about 0.2% to about 1%, by weight of the composition.

The second cationic polymers have a cationic charge density of at least about 4 meq/gm or at least about 4.5 meq/gm, and they have a molecular weight of at least about 500,000 to about 5,000,000, more preferably from about 500,000 to about 2,000,000.

In one embodiment, the second cationic polymers are water soluble or dispersible, non-crosslinked, synthetic cationic polymers having the following structure:

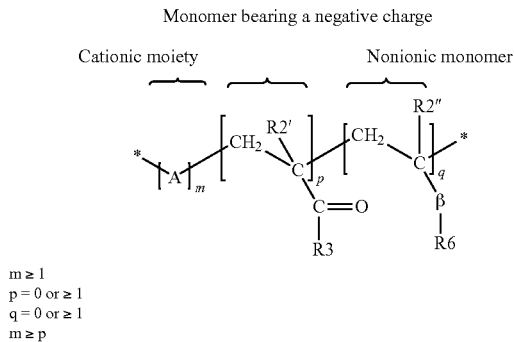

$m \geq 1$
$p = 0$ or $\geq 1$
$q = 0$ or $\geq 1$
$m \geq p$

Where A, may be one or more of the following cationic moieties:

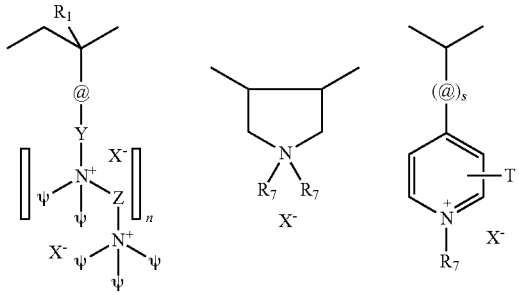

Where @ = amido, alkylamido, ester, ether, alkyl or alkylaryl.
Where Y = C1-C22 alkyl, alkoxy, alkylidene, alkyl or aryloxy
Where ψ = C1-C22 alkyl, alkyloxy, alkyl aryl or alkyl aryloxy
Where Z = C1-C22 alkyl, alkyloxy, aryl or aryloxy
Where R1 = H, C1-C4 linear or branched alkyl
Where s = 0 or 1, n = 0 or $\geq 1$
Where T and R7 = C1-C22 alkyl
Where X- = halogen, hydroxide, alkoxide, sulfate or alkylsulfate Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Preferred cationic monomers comprise quaternary ammonium group of formula —NR3+, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Preferred cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

More preferred cationic monomers include trimethyl ammonium propyl (meth)acrylamido chloride.

Where the monomer bearing a negative charge is defined by R2'=H, C1-C4 linear or branched alkyl and R3 as:

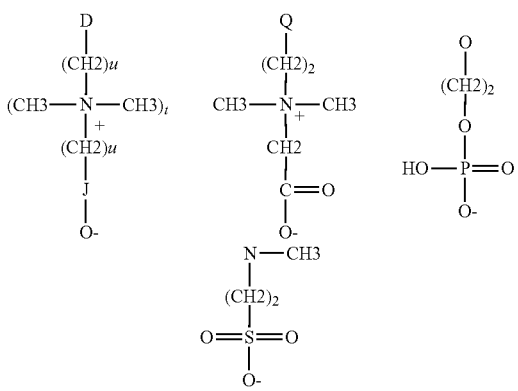

Where D = electronegative element chosen between oxygen, nitrogen, sulfur
Where Q = NH2 or O
Where u = 1-6
Where t = 0-1
Where J = oxygenated functional group containing the following elements P, S, C Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Preferred monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Where the nonionic monomer is defined by R2"=H, C1-C4 linear or branched alkyl, R6=linear or branched alkyl, alkyl aryl, aryl oxy, alkyloxy, alkylaryl oxy and β is defined as

Where G' and G" are, independently of one another, O, S or N—H and L=0 or 1.

Examples of such nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Preferred nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion ($X^-$) in association with the synthetic cationic polymers may be any known counterion so long as the polymers remain soluble or dispersible in water, in the personal care composition, or in a coacervate phase of the personal care composition, and so long as the counterions are physically and chemically compatible with the essential components of the personal care composition or do not otherwise unduly impair product performance, stability or aesthetics. Non limiting examples of such counterions include halides (e.g., chlorine, fluorine, bromine, iodine), sulfate and methylsulfate.

Optional Ingredients

The present personal care composition may further comprise optional ingredients selected from the group consisting of oily conditioning agents, hydrocarbon oils, polyolefins, fatty esters, fluorinated conditioning compounds, fatty alcohols, quaternary ammonium compounds, polyethylene glycols, anti-dandruff actives, anti-microbial actives, inorganic or synthetic particles, opacifying agents, suspending agents, propellants, paraffinic hydrocarbons, mono or divalent salts, fragrances, vitamins, chelating agents, colorants, pigments, dyes and mixtures thereof. These optional components are described in detail in U.S. Patent Publication No. 2003/0223951A1.

Silicone Conditioning Agent

If oily conditioning agents are included, they are preferably in the form of a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. Nos. 5,104,646, and 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 5,000 to about 1,500,000 csk, more preferably from about 10,000 to about 1,000,000 csk.

In one embodiment of the present invention, the personal care composition is opaque. The personal care composition comprises a non-volatile silicone oil having a particle size as measured in the personal care composition from about 1 μm to about 50 μm. The lyotropic liquid crystal coacervate, described herein, enhances deposition of these large particle size silicones (larger than about 1 μm).

In another embodiment of the present invention, the personal care composition comprises a non-volatile silicone oil having a particle size as measured in the personal care composition from about 100 nm to about 1 μm. A substantially clear composition embodiment of the present invention comprises a non-volatile silicone oil having a particle size as measured in the personal care composition of less than about 100 nm. The isotropic coacervate, described herein, enhances deposition of small particle size silicones having a particle size of less than or equal to about 1 μm.

Non-volatile silicone oils suitable for use in compositions of the present invention may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment of the present invention, the non-volatile silicone oil is polydimethylsiloxane.

Silicone fluids suitable for use in the compositions of the present invention are disclosed in U.S. Pat. Nos. 2,826,551; 3,964,500; and 4,364,837, British Patent No 849,433, and Silicon Compounds, Petrarch Systems, Inc. (1984).

Method of Making

All exemplified amounts are listed as weight percents and exclude minor materials such as diluents, preservatives, color solutions, imagery or conceptual ingredients, botanicals, and so forth, unless otherwise specified.

One method of making the present compositions involves mixing water and cocamide, which are heated to above 55° C. in the main mix tank. A polymeric anionic thickener, such as acrylates copolymer may optionally be added. Acrylates copolymer, which is commercially sold under the trade name, Aqua SF1, is available from National Starch and other commercial suppliers. Surfactants are then added and the pH is raised to >6.5 in order to activate thickening of the acrylates copolymer. Next, the synthetic cationic polymer is mixed, in a concentrated salt solution, with an anionic surfactant to form a liquid crystal coacervate in a premix. This premix is then added to the main mix tank. Then naturally derived cationic polymer is added to the main mix tank. Alternately, the naturally derived cationic polymer may be added to the main mix tank, followed by the aforementioned premix. It has been discovered that if the naturally derived cationic polymer is added to the main mix tank before the synthetic cationic polymer, then liquid crystal coacervate formation is inhibited, unless the synthetic cationic polymer is subsequently added to the main mix tank in the form of the aforementioned premix. Glycol distearate can be crystallized in a separate surfactant premix and then added to the main mix. A silicone/surfactant premix can be made to achieve the desired particle size and then added to the main mix tank. The pH is finally adjusted to the desired level and preservatives and minors added.

If acrylates copolymer is not used then the step of increasing the pH to >6.5 is not needed.

If a multiple phase shampoo is formulated, the multiple phases are made separately and then added separately to the package to achieve the desired appearance. The multiple phases may differ in color, composition, texture, transparency or mixtures of these attributes. Multiple phase personal care compositions are described in detail in U.S. Pat. No. 3,932,610.

The following examples are representative of shampoo compositions of the invention. The present compositions may comprise one, two, or more phases in accordance with the examples below:

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

| Ingredient (Phase 1) | Chem Conc. % | % Active in Final | | | % Active (Phase 1) | | |
|---|---|---|---|---|---|---|---|
| Sodium Laureth Sulfate (28% active in water) | 28.0 | 5.0000 | | 5.0000 | 5.0000 | 5.0000 | 4.0000 |
| Sodium Lauryl Sulfate (29% active in water) | 29.0 | 9.0000 | | 15.0000 | 15.0000 | 9.0000 | 8.0000 |
| Ammonium Laureth Sulfate (25% active in water) | 25.0 | | 10.0000 | | | | |
| Ammonium Lauryl Sulfate (25% active in water) | 25.0 | | 6.0000 | | | | |
| Polydimethyl siloxane | 100.0 | 1.0000 | 2.0000 | 1.5000 | 3.0000 | 4.0000 | 3.0000 |
| Glycol distearate | 100.0 | 1.5000 | 1.5000 | 1.5000 | 1.5000 | 1.5000 | 1.5000 |
| Carbopol Aqua SF-1 (Acrylates copolymer) (Available from National Starch) | 30.0 | | | | 1.5000 | 1.2500 | 1.2500 |
| Polyquaternium 10 (LR400) (Available from Americhol) | | 0.5000 | | | | | |
| Polyquaternium 10 (LR30M) (Available from Americhol) | | | 0.2500 | 0.2500 | 0.2500 | | |
| Polyquaternium 10 (KG30M) (Available from Americhol) | 100.0 | | | | | 0.5000 | 0.2500 |
| Mirapol 100 (Polyquaternium 6) (Available from Rhodia) | 31.5 | 0.0500 | | | | 0.2500 | 0.2500 |
| Polycare 133 (Polymethacryamidopropyl trimonium CL) (Available from Rhodia) | | | 0.1000 | 0.1000 | 0.1000 | | |
| cocodimethyl amide | 85.0 | 0.8000 | 0.8000 | 0.8000 | 0.8000 | 0.8000 | 0.8000 |
| Brij 30 (Laureth-4) | 100.0 | 1.0000 | 1.0000 | 1.0000 | 1.0000 | 1.0000 | 1.0000 |
| NaOH (50%) | 50.0 | as needed | as needed | as needed | as needed | as needed | as needed |
| Sodium Benzoate | 100.0 | 0.2500 | 0.2500 | 0.2500 | 0.2500 | 0.2500 | 0.2500 |
| Disodium EDTA | 100.0 | 0.1274 | 0.1274 | 0.1274 | 0.1274 | 0.1274 | 0.1274 |
| Citric Acid | 100.0 | 0.5000 | 0.5000 | 0.5000 | 0.5000 | 0.5000 | 0.5000 |
| NaCl | 100.0 | as needed | as needed | as needed | as needed | as needed | as needed |
| Sodium Xylene Sulfonate | 41.5 | as needed | as needed | as needed | as needed | as needed | as needed |
| Kathon CG (Methylchloroisothiazolinone and Methylisothiazolinone) | 100.0 | 0.0005 | 0.0005 | 0.0005 | 0.0005 | 0.0005 | 0.0005 |
| Perfume/colors/other minors | 100.0 | as needed | as needed | as needed | as needed | as needed | as needed |
| Q.S. Water-USP Purified | 100.0 | | | | | | |

| Ingredient (Phase 2) | Chem Conc. % | No 2nd Phase | % Active (Phase 2) | | |
|---|---|---|---|---|---|
| Sodium Laureth Sulfate (28% active in water) | 28.0 | | 5.0000 | 5.0000 | 4.0000 |
| Sodium Lauryl Sulfate (29% active in water) | 29.0 | | 15.0000 | 9.0000 | 8.0000 |
| Polydimethyl siloxane | 100.0 | | 1.0000 | 2.0000 | 1.0000 |
| Carbopol Aqua SF-1 (Acrylates copolymer) (Available from National Starch) | 30.0 | | 1.5000 | 1.2500 | 1.2500 |
| Polyquaternium 10 (LR30M) (Available from Americhol) | | | 0.2500 | | |
| Polyquaternium 10 (KG30M) (Available from Americhol) | 100.0 | | | 0.5000 | 0.2500 |
| Mirapol 100 (Polyquaternium 6) | 31.5 | | | 0.2500 | 0.2500 |
| Polycare 133 (Polymethacryamidopropyl trimonium CL) | | | 0.1000 | | |
| cocodimethyl amide | 85.0 | | 0.8000 | 0.8000 | 0.8000 |
| Brij 30 (Laureth-4) | 100.0 | | 1.0000 | 1.0000 | 1.0000 |
| NaOH (50%) | 50.0 | | as needed | as needed | as needed |
| Sodium Benzoate | 100.0 | | 0.2500 | 0.2500 | 0.2500 |
| Disodium EDTA | 100.0 | | 0.1274 | 0.1274 | 0.1274 |
| Citric Acid | 100.0 | | 0.5000 | 0.5000 | 0.5000 |
| NaCl | 100.0 | | as needed | as needed | as needed |
| Sodium Xylene Sulfonate | 41.5 | | as needed | as needed | as needed |
| Kathon CG (Methylchloroisothiazolinone and Methylisothiazolinone) | 100.0 | | 0.0005 | 0.0005 | 0.0005 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
 a) from about 5% to about 50% by weight of an anionic surfactant;
 b) from about 0.025% to about 5% by weight of a first cationic polymer wherein said first cationic polymer is polyquaternium-10 and wherein said first cationic polymer forms an isotropic coacervate in the neat composition or upon dilution with water;
 c) from about 0.025% to about 5% by weight of a second cationic polymer selected from the group consisting of polyquaternium 6, polymethacryamidopropyl trimonium chloride and mixtures thereof, wherein said second cationic polymer forms a lyotropic liquid crystal coacervate upon combination with said anionic surfactant; and
 d) from about 20% to about 94% by weight of water.

2. A personal care composition according to claim 1, further comprising an optional ingredient selected from the group consisting of oily conditioning agents, hydrocarbon oils, polyolefins, fatty esters, fluorinated conditioning compounds, fatty alcohols, quaternary ammonium compounds, polyethylene glycols, anti-dandruff actives, anti-microbial actives, inorganic or synthetic particles, opacifying agents, suspending agents, propellants, paraffinic hydrocarbons, mono or divalent salts, fragrances, vitamins, chelating agents, colorants, pigments, dyes and mixtures thereof.

3. A personal care composition according to claim 2, wherein said oily conditioning agent is a silicone conditioning agent having a particle size of from about 1 μm to about 50.

4. A personal care composition according to claim 2, wherein said oily conditioning agent is a silicone conditioning agent having a particle size of less than about 1 μm.

5. A personal care composition according to claim 2, wherein said oily conditioning agent is polydimethylsiloxane.

6. A personal care composition according to claim 1, wherein said composition is a multiple phase composition.

* * * * *